United States Patent [19]

Bock et al.

[11] Patent Number: 4,724,237

[45] Date of Patent: Feb. 9, 1988

[54] 2-SUBSTITUTED-AMINOMETHYL-1,4-BENZODIAZEPINES

[75] Inventors: Mark G. Bock; Roger M. Freidinger, both of Hatfield, Pa.

[73] Assignee: Merck & Co., Inc., Rahway, N.J.

[21] Appl. No.: 624,842

[22] Filed: Jun. 26, 1984

[51] Int. Cl.$^4$ .................... A61K 31/55; C07D 243/16
[52] U.S. Cl. ...................................... 514/221; 540/573
[58] Field of Search ...................... 260/244.4; 514/221; 540/573

[56] References Cited

U.S. PATENT DOCUMENTS

| | | | |
|---|---|---|---|
| 4,325,957 | 4/1982 | Zeugner et al. | 260/239 BD X |
| 4,497,740 | 2/1985 | Zeugner et al. | 260/244.4 |
| 4,533,662 | 8/1985 | Zeugner et al. | 514/221 |

FOREIGN PATENT DOCUMENTS 2952279  6/1981  Fed. Rep. of Germany ...... 514/221

OTHER PUBLICATIONS

BF839,365 Abstract, Chemical Abstracts, vol. 87, (1977) Entry 23345b.
Ann. Repts. Med. Chem., vol. 17, 1982, pp. 31–33, A. J. Prang et al.
Eating and its Disorders, 1984, p. 67, A. J. Stunkard et al.
Am. J. Physiol, vol. 242, 1982, p. G161, N. Barlos et al.
Biochem. Biophys. Acta, vol. 761, 1983, p. 269, R. T. Jensen et al.
Biochim. Biophys. Acta, vol. 757, 1983, p. 250, R. T. Jensen et al.
Eur. J. Pharmacol., vol. 87, 1983, p. 503, H. Kley et al.
Eur. J. Pharmacol., vol. 93, 1983, p. 265, J. E. Morley et al.
Mol. Pharmacol., vol. 17, 1980, p. 268, P. Robberecht et al.
Life Sci., vol. 30, 1982, p. 479, J. E. Morley.
Eur. J. Med. Chem., vol. 11, 1976, p. 501.
Nature, vol. 198, 1982, p. 759, D. Roemer et al.
Gastrointestinal Hormones, Raven Press, N.Y. G. B. J. Blass, Ed. 1980, p. 169, V. Mutt.
Proc. Natl. Acad. Sci. USA, vol. 78, 1981, p. 6304, W. F. Hahne et al.
Biomed. Res., vol. 3, 1982, p. 107, J. A. Williams.
Biochem. J., vol. 125, 1971, p. 678, Jorpes.
Tetrahedron, vol. 33, 1977, pp. 2725–2736, S. W. Willen et al.
J. Biol. Chem., vol. 258, 1983, p. 6746, M. Spanarkel et al.

Primary Examiner—Donald G. Daus
Assistant Examiner—William A. Teoli, Jr.
Attorney, Agent, or Firm—Richard A. Elder; Hesna J. Pfeiffer; Samuel B. Abrams

[57] ABSTRACT

Novel 2-substituted-aminomethyl-1,4-benzodiazepines which have been found to be antagonists of the function of cholecystokinins (CCK), to the preparation of these compounds, and to the use of these compounds to antagonize the function of CCK, which antagonism is useful, e.g., for the treatment and prevention of disorders of the gastrointestinal, central nervous and appetite regulatory systems of mammals, especially of humans.

9 Claims, No Drawings

2-SUBSTITUTED-AMINOMETHYL-1,4-BENZODIAZEPINES

The present invention is directed to novel 2-substituted-aminomethyl-1,4-benzodiazepines which have been found to be antagonists of the function of cholecystokinins (CCK), to the preparation of these compounds, and to the use of these compounds to antagonize the function of CCK, which antagonism is useful, e.g., for the treatment and prevention of disorders of the gastrointestinal, central nervous and appetite regulatory systems of mammals, especially of humans.

BACKGROUND OF THE INVENTION

Cholecystokinins (CCK) are neuropeptides (see, Mutt and Jorpes, *Biochem. J.*, 125, 678 (1971)) which exist in both gastrointestinal tissue and the central nervous system (V. Mutt, *Gastrointestinal Hormones*, G. B. J. Glass, ed., Raven Press, N.Y., 1980, p. 169), and include e.g., CCK-33, a neuropeptide of thirty-three aminoacids and its carboxylterminal octapeptide, CCK-8. These molecules are believed to be physiological satiety hormones and, therefore, may play an important role in appetite regulation (G. P. Smith, *Eating and Its Disorders*, A. J. Stunkard and E. Stellar, Eds., Raven Press, New York, 1984, p. 67).

In addition, CCK's stimulate colonic motility, gall bladder contraction, and pancreatic enzyme secretion, and inhibit gastric emptying. CCK's reportedly also co-exist with dopamine in certain mid-brain neurons, and thus may additionally play a role in the functioning of dopaminergic systems in the brain, as well as serve as neurotransmitters in their own right. See: A. J. Prange et al., "Peptides in the Central Nervous System", *Ann. Repts. Med. Chem.*, 17, 31, 33 (1982), and references cited therein; J. A. Williams, *Biomed. Res.*, 3, 107 (1982); and J. E. Morley, *Life Sci.*, 30, 479 (1982).

Antagonists to CCK have been useful for preventing or treating CCK-related disorders of the gastrointestinal, central nervous and appetite regulatory systems of mammals, especially of humans. Three distinct chemical classes of CCK-receptor antagonists have been reported. The first class comprises derivatives of cyclic nucleotides, of which dibutyryl cyclic GMP has been shown to be the most potent by detailed structure-function studies (see, N. Barlos et al., *Am. J. Physiol.*, 242, G161 (1982) and P. Robberecht et al., *Mol. Pharmacol.*, 17, 268 (1980)). The second class comprises peptide antagonists which are C-terminal fragments and analogs of CCK, of which both shorter (Boc-Met-Asp-Phe-NH$_2$, Met-Asp-Phe-NH$_2$) and longer (Cbz-Tyr(SO$_3$H)-Met-Gly-Trp-Met-Asp-NH$_2$) C-terminal fragments of CCK can function as CCK antagonists, according to recent structure-function studies (see, R. T. Jensen et al., *Biochim. Biophys. Acta.*, 757, 250 (1983), and M. Spanarkel et al., *J. Biol. Chem.*, 258, 6746 (1983)). Then the third class of CCK receptor antagonists comprises the amino acid derivatives: proglumide, a derivative of glutaramic acid, and the N-acyl tryptophans, including para-chlorobenzoyl-L-tryptophan (benzotript), (see, W. F. Hahne et al., *Proc. Natl. Acad. Sci. U.S.A.*, 78, 6304 (1981) and R. T. Jensen et al., *Biochim. Biophys. Acta.*, 761, 269 (1983)). All of these compounds, however, are relatively weak antagonists of CCK (IC$_{50}$: generally 10$^{-4}$M, but down to 10$^{-6}$M in the case of the peptides) and the peptide CCK-antagonists have substantial stability and absorption problems.

It was, therefore, an object of this invention to identify substances which more effectively antagonize the function of cholecystokinins in disease states in mammals, especially in humans. It was another object of this invention to prepare novel compounds which inhibit cholecystokinins and which display opiate agonism and analgesic activity. It was still another object of this invention to develop a method of preparing these novel cholecystokinin-antagonists. It was also an object of this invention to develop a method of antagonizing the function of cholecystokinins in disease states in mammals. It was still a further object of this invention to develop a method of preventing or treating disorders of the gastrointestinal, central nervous and appetite regulatory systems of mammals, especially of humans.

SUMMARY OF THE INVENTION

The instant invention is directed to certain 2-substituted-aminomethyl-1,4-benzodiazepines, which have been found to be antagonists of the function of cholecystokinins (CCK), to the preparation of these compounds, and to the use of these compounds in the treatment and prevention of disorders of the gastrointestinal, central nervous and appetite regulatory systems of mammals, especially of humans.

DETAILED DESCRIPTION OF THE INVENTION

The 2-substituted-aminomethyl-1,4-benzodiazepines of this invention are those of formula I:

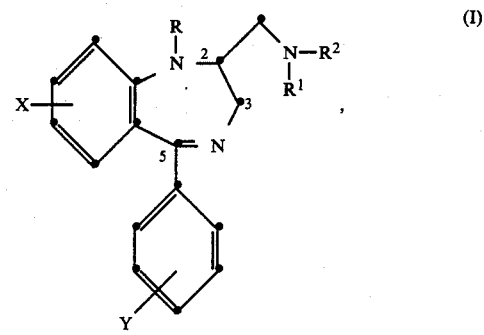

wherein:
X=one or two of the substituents: F, Cl or Br; C$_1$–C$_4$-straight- or branched-chain alkyl, including methyl, ethyl, propyl, isopropyl, butyl, isobutyl, and t-butyl; C$_1$–C$_4$-alkoxy; C$_1$–C$_4$-alkylthio; hydroxy; nitro; cyano; amino; or trifluoromethyl, and may be attached at either or both the 7- and/or 8-positions;

Y=independently, the same as X, and may be attached at any of positions 2-6 on the aromatic ring;

R=H, C$_1$–C$_4$-alkyl, cyclo-C$_3$–C$_5$-alkyl, C$_1$–C$_4$-alkenyl, or acetyl;

R$^1$=H, C$_1$–C$_4$-alkyl or cyclo-C$_3$–C$_5$-alkyl;

R$^2$ = unsubstituted, or mono- or disubstituted phenyl, where the substituents are as defined under X, above;

= —CH—R$^3$,
      |
      CO$_2$R$^4$ where R$^3$ = (CH$_2$)$_n$—C$_1$–C$_4$—alkyl,
—(CH$_2$)$_n$—2-indole,
—(CH$_2$)$_n$—3-indole, or
—(CH$_2$)$_n$—phenyl (unsubstituted or -continued mono- or disubstituted, where the substituents are as defined for X, above);

n = 0-4; and

R⁴ = H or $C_1$-$C_4$—alkyl; or

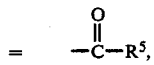

where $R^5$ = —CH—R⁶, wherein R⁶ =
    |
    NHR⁷

($CH_2$)$_n$—2-indole or
($CH_2$)$_n$—3-indole, where n = 0-4;

and $R^7$ = H, COOR⁸, or —C(O)R⁸, where $R^8$ = $C_1$-$C_4$—alkyl;

= —($CH_2$)$_m$SCH₂NHCOCH₃, where m = 1-4;

= $C_1$-$C_4$—alkyl;

= pyrazine (unsubstituted or monosubstituted where the substituents may be Cl, COOR⁸, CN or NO₂), wherein R⁸ is as defined above;

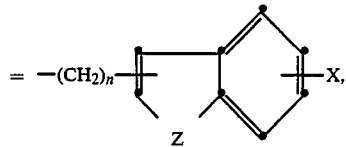

wherein Z = O, S or NR, ($CH_2$)$_n$ is attached at the 2- or 3-position, and R, n and X are as defined above;

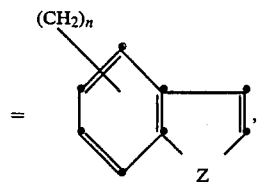

wherein ($CH_2$)$_n$ is attached at the 4- or 5-position, and n and Z are as defined above;

= ($CH_2$)$_m$CO₂CH₂phenyl, wherein m is as defined above;

= —O—$C_1$-$C_4$—alkyl;

= —CHOHC₆H₅; or

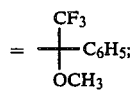

or of the formula II:

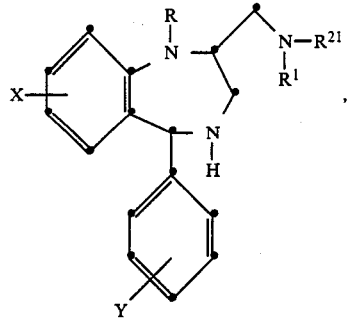

wherein:

X Y, R and R¹ are as defined above; and $R^{21}$=$R^2$ as defined above, including wherein R⁵, as defined above, also=pyridine,

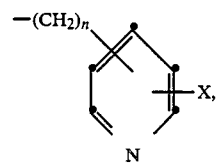

where ($CH_2$)$_n$ is attached at the 2-, 3- or 4-position and n and X are as defined above;

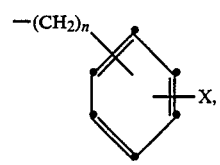

where the point of attachment is at any position on the ring and n and X are as defined above; or

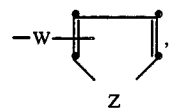

where the point of attachment is at the 2- or 3-position and W=H, straight or branched chain $C_1$-$C_4$-alkyl or $C_1$-$C_4$-alkoxy, nitro, F, Cl or Br, and Z is as defined above, the optical isomers of formula I, or pharmaceutically-acceptable salts of the compounds of formulae I or II.

Preferred compounds of formula I according to the instant invention include those in which X is F or Cl; R is H or $C_1$-$C_4$-alkyl; R¹ is H; R² is

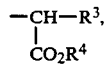

wherein R³ is -($CH_2$)-phenyl or ($CH_2$)-2 or 3-indole, and R⁴ is $C_1$-$C_4$-alkyl; or R² is

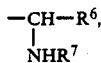

where $R^6$ is $(CH_2)$-2-indole or $(CH_2)$-3-indole and $R^7$ is H, $COOR^8$, or

wherein $R^8$ is $C_1-C_4$-alkyl; or $R^5$ is

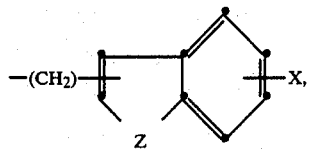

wherein Z is O, S or NR and X and R are as defined above; or $R^5$ is

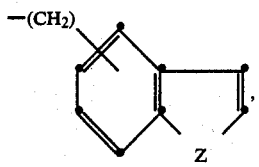

wherein Z is as defined above; or $R^5$ is -CHOHC$_6$H$_5$.

Preferred compounds of formula II according to the instant invention include those in which X is F or Cl; R is H or $C_1-C_4$-alkyl; $R^1$ is H; $R^2$ is

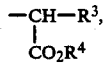

wherein $R^3$ is -(CH$_2$)-phenyl or (CH$_2$)-2 or 3-indole, and $R^4$ is $C_1-C_4$-alkyl; or $R^2$ is

wherein $R^5=$

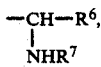

where $R^6$ is (CH$_2$)-2-indole or (CH$_2$)-3-indole and $R^7$ is H, COOR$^8$, or

wherein $R^8$ is $C_1-C_4$-alkyl; or $R^5$ is

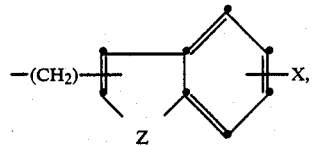

wherein Z is O, S or NR and X, R and n are as defined above; or $R^5$ is

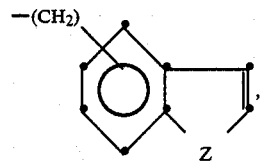

wherein Z is as defined above; or $R^5$ is -CHOHC$_6$H$_5$; or $R^5$ is

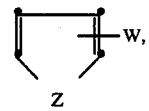

wherein W and Z are as defined above; $R^5$ is

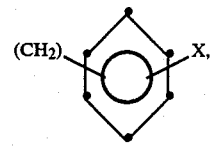

wherein X is as defined above.

Particularly preferred compounds of formula I include 1-methyl-2-(2'-indolecarbonyl)aminomethyl-5-(2'-fluorophenyl)-2,3-dihydro-1H-1,4-benzodiazepine, 1-methyl-2-(4-thianaphthenemethylcarbonyl)aminomethyl-5-(2'-fluorophenyl)-2,3-dihydro-1H-1,4-benzodiazepine 1-methyl-2-(2-L-hydroxy-2-phenylacetyl)aminomethyl-5-(2'-fluorophenyl)-2,3-dihydro-1H-1,4-benzodiazepine, 1-methyl-2-[1-(S)-1-methoxycarbonyl-2-phenylethylamino] methyl-5-(2'-fluorophenyl)-2,3-dihydro-1H-1,4-benzodiazepine, 1-methyl-2-(3'-trifluoromethylphenyl)aminomethyl-5-(2'-fluorophenyl)-2,3-dihydro-1H-1,4-benzodiazepine, 1-methyl-2-[2-((1,1-dimethylethoxy)carbonyl)amino-3-(1H-indol-3-yl)propanoyl]aminomethyl-5-(2'-fluorophenyl)-2,3-dihydro-1H-1,4-benzodiazepine, 1-methyl-2-[(2-methylpropoxy)carbonyl]aminomethyl-5-(2'-fluorophenyl)-2,3-dihydro-1H-1,4-benzodiazepine, 1-methyl-2-[2-amino-3-(1H-indol-3-yl)propanoyl]aminomethyl-5-(2'-fluorophenyl)-2,3-dihydro-1H-1,4-benzodiazepine, 1-methyl-2-(2-methoxy-2-trifluoromethyl-2-phenylacetyl)aminomethyl-5-(2'-fluorophenyl)-2,3-dihydro-1H-1,4-benzodiazepine, 1-methyl-2-[2-(S)-((1,1-dimethylethoxy)carbonyl)amino-3-acetamidomethylmercaptopropanoyl]aminomethyl-5-(2'-fluorophenyl)-2,3-dihydro-1H-1,4-benzodiazepine, 1-methyl-2-benzylsuccinoylaminomethyl-5-(2'-fluorophenyl)2,3-dihydro-1H-1,4-benzodiazepine, and 1-methyl-2-(acetamidomethylmercaptoacetyl)aminomethyl-5-(2'-fluorophenyl)-2,3-dihydro-1H-1,4-benzodiazepine.

Particularly preferred compounds of formula II include 1-methyl-2-(2'-indolecarbonyl)aminomethyl-5-(2'-fluorophenyl)-2,3,4,5-tetrahydro-1H-1,4-benzodiazepine, 1-methyl-2-(4-thianaphthenemethylcarbonyl)aminomethyl-5-(2'-fluorophenyl)-2,3,4,5-tetrahydro-1H-1,4-benzodiazepine, 1-methyl-2-(2-L-hydroxy-2-phenylacetyl)aminomethyl-5-(2'-fluorophenyl)-2,3,4,5-tetrahydro-1H-1,4-benzodiazepine, 1-methyl-2-(1H-indol-3-yl)methylcarbonylaminomethyl-5-(2'-fluorophenyl)-2,3,4,5-tetrahydro-1H-1,4-benzodiazepine, 1-methyl-2-(3-thiophenecarbonyl)aminomethyl-5-(2'-fluorophenyl)-2,3,4,5-tetrahydro-1H-1,4-benzodiazepine, and 1-methyl-2-p-chlorobenzoylaminomethyl-5-(2'-fluorophenyl)-2,3,4,5-tetrahydro-1H-1,4-benzodiazepine and 1-methyl-2-o-fluorobenzoylaminomethyl-5-(2'-fluorophenyl)-2,3,4,5-tetrahydro-1H-1,4-benzodiazepine.

The pharmaceutically-acceptable salts of the compounds of the instant invention include the conventional non-toxic salts or the quarternary ammonium salts of the compounds of this invention formed, for example, from non-toxic inorganic or organic acids. For example, such conventional non-toxic salts include those derived from inorganic acids, such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, theophylline, 8-chlorotheophylline, p-aminobenzoic, p-acetamidobenzoic, methanesulfonic, ethane disulfonic, oxalic, isethionic, and the like.

Certain 2-acylaminomethyl-1H-2,3-dihydro-1,4-benzodiazepine derivatives were disclosed in U.S. Pat. No. 4,325,957. However, those derivatives were suggested as simply possessing strong analgesic activities, in addition to psychopharmacological, diuretic and antiarrythmic properties. Additionally, the compound, where X=H, Y=2-F, R=CH$_3$, R$^1$=H and R$^2$=thiophene-3-carbonyl, has been reported to be an opiate-agonist with selectivity for the kappa receptor (see, D. Roemer et al., Nature, 298, 759 (1982)) and its (—)-enantiomer is preferred for high analgesic activity (see, H. Kley et al., Eur. J. Pharmacol., 87, 503 (1983)). This compound has also been shown to increase food intake in rats (See J. E. Morley et al., Eur. J. Pharmacol., 93, 265 (1983)). However, none of the compounds of the instant invention has been previously disclosed or suggested and it has not been previously suggested that even the previously-known, related compounds would antagonize the function, particularly the excessive function, of cholecystokinins in a disease state in mammals.

Compounds according to formula (I) of the instant invention may be produced by either of two methods, viz:

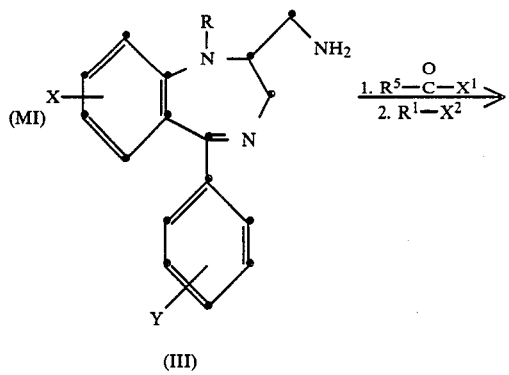

(III)

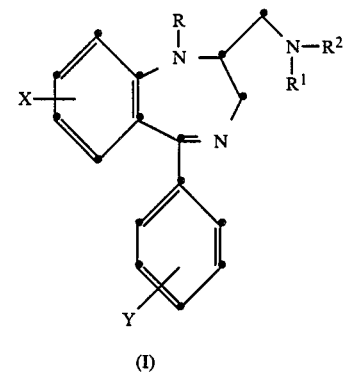

(I)

wherein X$^1$=OH, Cl,

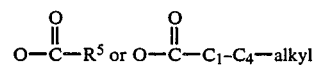

and X$^2$=Cl, Br, I, OSO$_2$C$_1$-C$_4$-alkyl, OSO$_2$-phenyl or OSO$_2$-substituted phenyl; or

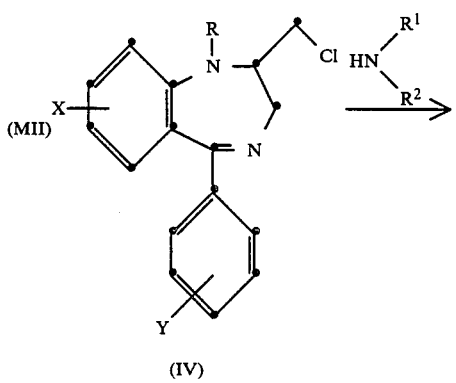

(IV)

-continued

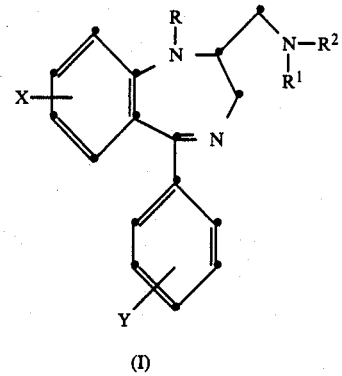

(I)

According to method MI, 2-substituted-aminomethyl-1,4-benzodiazepine derivatives of formula I may be prepared by acylating an amino compound of formula III, or an acid addition salt thereof, with a carbonic acid or a reactive carbonic acid derivative. (The preparation of 2-aminomethyl-1,4-benzodiazepine derivatives of formula III which are used as starting materials in the present invention may be carried out in a known manner according to processes described in U.S. Pat. No. 4,325,957 and German Offenlegungsschrift No. 2,221,558.) The acylation is carried out in an aprotic solvent at temperatures between −30° C. and the boiling point of the solvent under normal atmospheric pressure.

If a carbonic acid halogenate or a carbonic acid anhydride is used as the acylating agent, the reaction is preferably carried out in the presence of an acid-binding agent, such as a tertiary amine, for example, triethylamine, pyridine, 4-dimethylaminopyridine and the like, or an alkali metal hydroxide or alkali metal carbonate, for example, sodium hydroxide, potassium carbonate, and the like. Examples of suitable inert solvents include N,N-dimethylformamide, chloroform, methylene chloride, tetrahydrofuran, dioxane, toluene and chlorobenzene.

The compounds of formula I may also be prepared by reacting a compound of formula III with a carbonic acid, $R^5\text{-}CO_2H$, in an inert solvent at temperatures of from −30° C. to the boiling point of the solvent, preferably at room temperature, in the presence of a suitable coupling reagent, such as dicyclohexylcarbodiimide, 1-ethyl-3-(3-dimethylaminopropyl)carbodiimide hydrochloride, carbonyldiimidazole, or the like.

Compounds of formula I, wherein $R^1$ represents hydrogen, may subsequently be converted into the corresponding N-alkyl compounds by alkylation in the conventional manner. For example, such alkylations may be effected by reacting compounds of formula I, wherein $R^1$ is hydrogen, with a metallating agent, such as sodium or potassium hydride, or alkyl lithium reagent, in an inert solvent at temperatures of −78° C. to the boiling point of the solvent. The metallated compound is then subsequently reacted with an alkyl halogenide, alkylsulfate or alkylsulfonic ester.

According to method MII, the compounds of formula I may alternatively be prepared by reacting a 2-halomethyl-1,4-benzodiazepine derivative of formula IV (prepared according to procedures in *Eur. J. Med. Chem.*, 11, 501 (1976) and U.S. Pat. No. 4,325,957) with an amine of the formula, $HNR^2R^1$, in an inert solvent at temperatures of 0° C. to the boiling point of the solvent, or without solvent, at temperatures of 0° C. to the boiling point of the amine, $HNR^2R^1$, in the presence of an acid-binding agent, such as an alkali metal hydroxide or alkali metal carbonate, as defined above.

Compounds according to formula II of the instant invention may be produced according to method MIII:

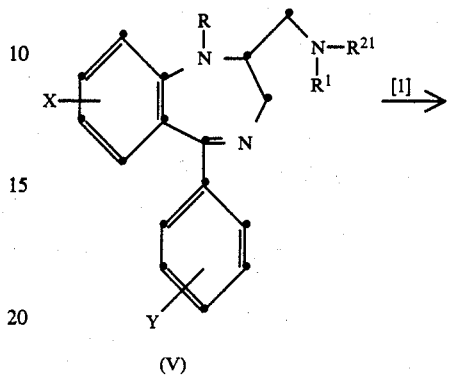

(V)

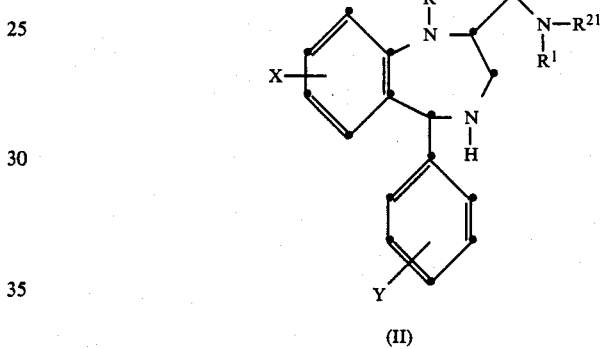

(II)

[1] NaBH$_3$CN, NaBH$_4$ or LiBH$_4$

According to method MIII, 2-substituted-aminomethyl-1,4-benzodiazepine derivatives of formula II may be prepared by dissolving a compound of formula V (prepared analogously to the preparation of compounds of formula III) in a suitable solvent, such as glacial acetic acid, methanol or ethanol, and the solution is cooled to −30° to +15° C. and treated with a suitable reducing agent, such as sodium cyanoborohydride, sodium borohydride, or lithium borohydride. The reaction mixture is stirred until completion of the reaction (approximately 5 minutes to 5 hours) and poured into water. The resulting reaction mixture is extracted with an organic solvent, such as ethyl acetate, chloroform or methylene chloride, and the combined organic extracts are washed with sodium bicarbonate solution and brine. Concentration affords the crude product which may be further purified by chromatography or recrystallization.

The pharmaceutically-acceptable salts of the present invention may be synthesized from the compounds according to the instant invention which contain a basic or acidic moiety by conventional chemical methods. Generally, the salts are prepared by reacting the free base or free acid with stoichiometric amounts of or with an excess of the desired salt-forming inorganic or organic acid or base in a suitable solvent or in various combinations of solvents. The pharmaceutically-acceptable salts of the acids according to this invention are also readily prepared by conventional procedures such as treating an acid of this invention with an appropriate amount of a base, such as an alkali or alkaline earth metal hydroxide, e.g., sodium, potassium, lithium, calcium, or magnesium, or an organic base such as an amine, e.g., dibenzylethylenediamine, triethylamine, piperidine, pyrrolidine, benzylamine, and the like.

In addition to the racemic forms of the compounds of formulae I and II produced according to the foregoing preparation methods, the present invention also includes the optically-active forms of these compounds which may be obtained from the racemic mixtures in a conventional manner by formation of the salts using suitable optically-active acids, such as tartaric acid, O,O'-dibenzoyl tartaric acid, mandelic acid or di-O-isopropylidene-2-oxo-L-gulonic acid, and fractionated crystallization of the optically active antipodes of the resulting salts (see, S. W. Willen et al., *Tetrahedron*, 33, 2725-2736 (1977)). The salts may be transformed into free bases which may be further transformed into the pharmacologically-acceptable salts, and the racemic mixtures, optically-active isomers and acid-addition salts may be purified by recrystallization from solvents, such as lower alkyl alcohols or ethers. The preferred stereochemical configuration of the 2-position of all compounds according to the instant invention for CCK-antagonism is that designated (S) when $R^1=H$.

Screening of the novel compounds according to the present invention to determine biological activity and obtain an $IC_{50}$ value for them, in order to identify significant CCK-antagonism, may be accomplished using an $^{125}I$-CCK receptor binding assay and in vitro isolated tissue preparations. These tests involve the following:

CCK receptor binding (pancreas) method

CCK-33 was radiolabeled with $^{125}I$-Bolton Hunter reagent (2000 Ci/mmole), as described by Sankara et al. (*J. Biol. Chem.*, 254, 9349-9351, 1979). Receptor binding was performed according to Innis and Snyder (*Proc. Natl. Acad. Sci.*, 77, 6917-6921, 1980), with the minor modification of adding the additional protease inhibitors, phenyl-methane sulfonyl fluoride and o-phenanthroline, which have no effect on the $^{125}I$-CCK receptor binding assay.

The whole pancreas of a male Sprague-Dawley rat (200-350 g), which had been sacrificed by decapitation, was dissected free of fat tissue and homogenized in 20 volumes of ice-cold 50 mM Tris HCl (pH 7.7 at 25° C.) with a Brinkmann Polytron PT-10. The homogenates were centrifuged at 48,000 g for 10 minutes, then the resulting pellets were resuspended in Tris Buffer, centrifuged as above, and resuspended in 200 volumes of binding assay buffer (50 mM Tris HCl, pH 7.7 at 25° C., 5 mM dithiothreitol, 0.1 mM bacitracin, 1.2 mM phenylmethane sulfonyl fluoride and 0.5 mM o-phenanthroline).

For the binding assay, 25 $\mu$l of buffer (for total binding), or unlabeled CCK-8 sulfate sufficient to give a final concentration of 1 $\mu$M of CCK-8 (for nonspecific binding), or the compounds of the formula of the compounds according to the instant invention (for determination of antagonism to $^{125}I$-CCK binding) and 25 $\mu$l of $^{125}I$-CCK-33 (30,000-40,000 cpm), were added to 450 $\mu$l of the membrane suspensions in microfuge tubes. All assays were run in duplicate or triplicate, and the reaction mixtures were incubated at 37° C. for 30 minutes and centrifuged in a Beckman Microfuge (4 minutes) immediately after adding 1 ml of ice-cold incubation buffer. The supernatant was aspirated and discarded, and the pellets were counted with a Beckman Gamma 5000. For Scatchard analysis to determine the mechanism of inhibition of $^{125}I$-CCK binding by the most potent compounds (*Ann. N.Y. Acad. Sci.*, 51, 660, 1949), $^{125}I$-CCK-33 was progressively diluted with increasing concentrations of CCK-33.

CCK receptor binding (brain) method

CCK-33 was radiolabeled and the binding was performed according to the description for the pancreas method, with modifications according to Saito et al., *J. Neurochem.*, 37, 483-490, 1981.

Male Hartley guinea pigs (300-500 g) were sacrificed by decapitation, and the brains were removed and placed in ice-cold 50 mM Tris HCl (Trizma-7.4) [pH 7.4 at 25° C.]. The cerebral cortex was dissected and used as a receptor source and each gram of fresh guinea pig brain tissue was homogenized in 10 ml of Tris/Trizma buffer with a Brinkman polytron PT-10. The homogenates were centrifuged at 42,000 g for 15 minutes, then the resulting pellets were resuspended in 80 volumes of binding assay buffer (10 mM N-2-hydroxy-ethyl-piperazine-N'-2-ethanesulfonic acid (HEPES), 5 mM $MgCl_2$, 1 mM ethylene glycol-bis-($\beta$-amino-ethyl-ether-N,N'-tetraacetic acid (EGTA), 0.4% BSA and 0.25 mg/ml bacitracin, pH 6.5).

The remainder of the binding assay method was as described for the pancreas method, except that the reaction mixtures were incubated at 25° C. for 2 hours before centrifugation.

In vitro effect of the compounds according to this invention on $^{125}I$-CCK-33 receptor binding The compounds of the instant invention inhibited specific $^{125}I$-CCK-33 binding in a concentration-dependent manner, generally with an $IC_{50}$ less than or equal to 100 $\mu$M.

An additional method of confirming competitive antagonism of CCK which may be used is the following:

Isolated guinea pig gall bladder method

The two halves of the gall bladders, free of adjacent tissue, of male Hartley guinea pigs (400-600 g), which had been sacrificed by decapitation, are suspended under 1 g tension along the axis of the bile duct in 5 ml organ bath, containing a Kreb's bicarbonate solution of 118 mM NaCl, 4.75 mM KCl, 2.54 $CaCl_2$, 1.19 mM $KH_2PO_4$, 1.2 mM $MgSO_4$, 25 mM $NaHCO_3$ and 11 mM dextrose, which is maintained at 32° C. and bubbled with a mixture of 95% $O_2$ and 5% $CO_2$. The tissues are washed every 10 minutes for 1 hour to obtain equilibrium prior to the beginning of the study and the isometric contractions of the strips are recorded using Statham (60 g:0.12 mm) strain gauges and a Hewlett-Packard 77588 recorder.

CCK-8 is added cumulatively to the baths and $EC_{50}$'s are determined using regression analysis. After washout (every 10 minutes for 1 hour), the compound to be tested is added at least 5 minutes before the addition of CCK-8 and the $EC_{50}$ of CCK-8 in the presence of compound to be tested is similarly determined.

A shift to the right of the CCK dose response curve without reduction of the maximal centractile response, indicates competitive antagonism of CCK from this method.

The ability of the compounds of the instant invention to antagonize CCK makes these compounds useful as pharmaceutical agents for mammals, especially for humans, for the treatment and prevention of disorders wherein CCK may be involved. Examples of such disease states include gastrointestinal disorders, especially such as irritable bowel syndrome or ulcers excess pancreatic or gastric secretion, acute pancreatis, or motility disorder; central nervous system disorders, caused by CCK interactions with dopamine, such as neuroleptic disorders, tardive dyskinesia, Parkinson's disease, psychosis or Gilles de la Tourette Syndrome; and disorders of appetite regulatory systems.

The compounds of the instant invention or pharmaceutically-acceptable salts thereof, may be administered to a human subject either alone or, preferably, in combination with pharmaceutically-acceptable carriers or diluents, in a pharmaceutical composition, according to standard pharmaceutical practice. The compounds can be administered orally or parenterally, including intravenous, intramuscular, intraperitoneal, subcutaneous and topical administration.

For oral use of an antagonist of CCK, according to this invention, the selected compounds may be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents include lactose and dried corn starch. When aqueous suspensions are required for oral use, the active ingredient is combined with emulsifying and suspending agents. If desired, certain sweetening and/or flavoring agents may be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

When a compound according to the instant invention, or a salt thereof, is used as an antagonist of CCK in a human subject, the daily dosage will normally be determined by the prescribing physician. Moreover, the dosage will vary according to the age, weight, and response of the individual patient, as well as the severity of the patient's symptoms. However, in most instances, an effective daily dosage will be in the range of from about 0.05 mg/kg to about 100 mg/kg, and preferably, of from 0.5 mg/kg to about 20 mg/kg, administered in single or divided doses. In some cases, however, it may be necessary to use dosages outside these limits.

The invention is further defined by reference to the following example which is intended to be illustrative and not limiting.

EXAMPLE 1

Preparation of 1-methyl-2-(2'-indolecarbonyl)aminomethyl-5-(2'-fluorophenyl)-2,3-dihydro-1H-1,4,-benzodiazepine.

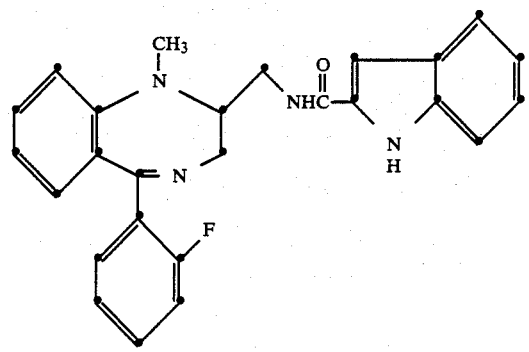

1-Methyl-2-aminomethyl-5-(2'-fluorophenyl)-2,3-dihydro-1H-1,4-benzodiazepine (250 mg, 0.88 mmole) and 2-indole carboxylic acid (142 mg, 0.88 mmole) were combined with 5 ml of dry methylene chloride, and 1-ethyl-3-(3-dimethylaminopropyl)carbodiimide hydrochloride (169 mg, 0.88 mmole) was added to this mixture at room temperature. The pH of the reaction mixture was adjusted to 8.5 with triethylamine and after overnight stirring, the reaction mixture was diluted with ethyl acetate (200 ml) and the organic phase was washed with saturated sodium bicarbonate solution and brine. Rotoevaporation of the dried (MgSO$_4$) extracts afforded 300 mg of an oil which was purified by silica gel chromatography (ethyl acetate-hexane elution, 2:1 v/v) to give the analytical sample (150 mg) which was 99% pure by HPLC.

MS (70 ev): 426 (M+), 253, 225, 144.

Pmr (CDCl$_3$): according to theory.

Elemental Analysis: C$_{26}$H$_{23}$FN$_4$O 0.2H$_2$O: Calc: N, 13.02; C, 72.60; H, 5.48 Found: N, 12.41; C, 72.75; H, 5.43.

EXAMPLE 2

Preparation of 1-methyl-2-(4-thianaphthenemethylcarbonyl)aminomethyl-5-(2'-fluorophenyl)-2,3-dihydro-1H-1,4-benzodiazepine

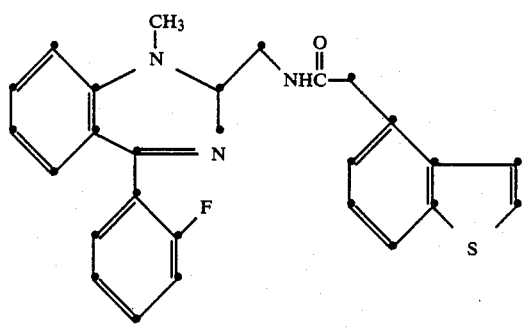

According to the method of Example 1 1-methyl-2-aminomethyl-5-(2'-fluorophenyl)-2,3-dihydro-1H-1,4-benzodiazepine (250 mg, 0.88 mmole) and 4-thianaphthene acetic acid (170 mg, 0.88 mmole) were combined with 4 ml of dry methylene chloride, and 1-ethyl-3-(3- dimethylaminopropyl)carbodiimide hydrochloride (169 mg, 0.88 mmole) was added to this mixture. After pH-adjustment, overnight stirring, dilution and washing, rotoevaporation of the dried extracts of the reaction afforded 300 mg of an oil which was purified by silica gel chromatography (ethyl acetate-hexane elution, 4:1 v/v) to give the analytical sample (100 mg) which was 88% pure by HPLC.

MS (FAB): 458 (M+ +H), 253, 147.

Pmr (CDCl$_3$): according to theory.

Elemental Analysis: $C_{27}H_{24}FN_3OS$ 0.2H$_2$: Calc: N, 9.11; C, 70.31; H, 5.33 Found: N, 8.82; C, 70.27; H, 5.27.

EXAMPLE 3

Preparation of 1-methyl-2-(2-L-hydroxy-2-phenylacetyl)aminomethyl-5-(2'-fluorophenyl)-2,3-dihydro-1H-1,4-benzodiazepine

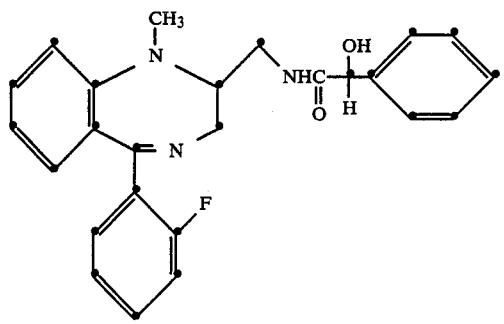

According to the method of Example 1, 1-methyl-2-aminomethyl-5-(2'-fluorophenyl)-2,3-dihydro-1H-1,4-benzodiazepine (500 mg, 1.76 mmole) and L-mandelic acid (268 mg, 1.76 mmole) were combined with 5 ml of dry methylene chloride, and 1-ethyl-3-(3-dimethylaminopropyl)carbodiimide hydrochloride (337 mg, 1.76 mmole) was added to this mixture. After pH-adjustment, overnight stirring, dilution (with 250 ml of ethyl acetate) and washing, rotoevaporation of the dried extracts of the reaction afforded 540 mg of an oil which was purified by silica gel chromatography (chloroform-ethanol-ammonia elution, 95:5:0.05 v/v/v) to give the analytical sample which was 94% pure by HPLC.

MS (20 ev): 417 (M+), 310, 253, 225.

Pmr (CDCl$_3$): according to theory.

Elemental Analysis: $C_{25}H_{24}FN_3O_2$ 0.2H$_2$O: Calc: N, 9.98; C, 71.30; H, 5.84 Found: N, 9.80; C, 71.31; H, 5.93.

EXAMPLE 4

Preparation of 1-methyl-2-(1H-indol-3-yl)methylcarbonylaminomethyl-5-(2'-fluorophenyl)-2,3-dihydro-1H-1,4-benzodiazepine hydrate

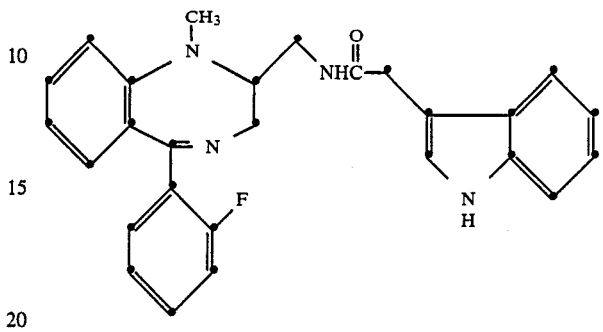

According to the method of Example 1, 1-methyl-2-aminomethyl-5-(2'-fluorophenyl)-2,3-dihydro-1H-1,4-benzodiazepine (250 mg, 0.88 mmole) and indole-3-acetic acid (154 mg, 0.88 mmole) were combined with 4 ml of dry methylene chloride, and 1-ethyl-3-(3-dimethylaminopropyl)carbodiimide hydrochloride (169 mg, 0.88 mmole) was added to this mixture. After pH-adjustment, overnight stirring, dilution and washing, rotoevaporation of the dried extracts of the reaction afforded 290 mg of an oil which was purified by silica gel chromatography (ethyl acetate elution) to give material which was 70% pure by HPLC. Rechromatography (chloroform-ethanol elution, 95:5 v/v) afforded the analytical sample, 93% pure, as a yellow solid.

MS (20 ev): 440 (M+), 253, 225, 130.

Pmr (CDCl$_3$): according to theory.

Elemental Analysis: $C_{27}H_{25}FN_4O$ H$_2$O: Calc: N, 12.22; C, 70.72; H, 5.93 Found: N, 12.23; C, 70.89; H, 5.62.

EXAMPLE 5

Preparation of 1-methyl-2-[1-(S)-1-methoxycarbonyl-2-phenylethylamino]methyl-5-(2'-fluorophenyl)-2,3-dihydro-1H-1,4-benzodiazepine

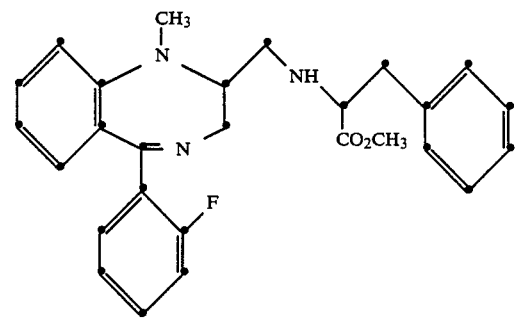

1-Methyl-2-chloromethyl-5-(2'-fluorophenyl)-2,3-dihydro-1H-1,4-benzodiazepine (150 mg, 0.5 mmole) and methyl-2(S)-amino-3-phenylpropionate (108 mg, 0.5 mmole) were combined in 4 ml of dry N,N-dimethylformamide, and potassium carbonate (138 mg, 1 mmole) and sodium iodide (70 mg, 0.5 mmole) were added to this mixture. The reaction mixture was protected from moisture and heated at 60° C. for 48 hours. The solvent was then removed under reduced pressure and the residue was partitioned between ethyl acetate (100 ml) and saturated sodium bicarbonate solution (50 ml). The phases were separated and the organic layer was washed with sodium bicarbonate solution and brine, then dried (MgSO4) and concentrated to yield 300 mg of crude product. The analytical product was obtained via chromatography on silica gel (ethyl acetate-hexane elution, 7:3 v/v) as a mixture of diasteriomers; 95% pure by HPLC.

MS (20 ev): 445 (M+), 253, 225, 212, 83.

Pmr (CDCl3): according to theory.

Elemental Analysis: $C_{27}H_{28}FN_3O_2$ 0.6H2O: Calc: N, 9.20; C, 71.05; H, 6.45 Found: N, 8.81; C, 71.01; H, 6.56.

EXAMPLE 6

Preparation of 1-methyl-2-(3'-trifluoromethylphenyl)aminomethyl-5-(2'-fluorophenyl)-2,3-dihydro-1H-1,4-benzodiazepine

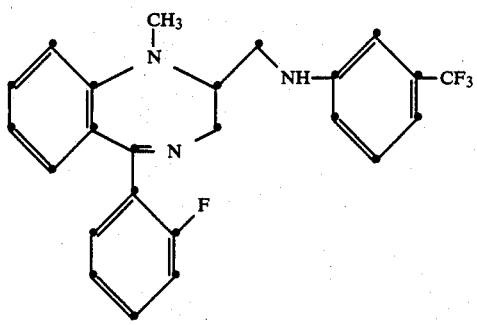

According to the method of Example 5, 1-methyl-2-chloromethyl-5-(2'-fluorophenyl)-2,3-dihydro-1H-1,4-benzodiazepine (200 mg, 0.66 mmole) and m-trifluoromethyl aniline (319 mg, 1.97 mmole) were combined in 2 ml of dry N,N-dimethylformamide, and potassium carbonate (273 mg, 1.97 mmole) and sodium iodide (198 mg, 1.32 mmole) were added to this mixture (which was heated at 65° C. for 18 hours). After solvent-removal, partitioning, separation, washing, drying and concentrating, the analytical product was obtained via chromatography on silica gel (ethyl acetate-hexane elution, 3:7 v/v) and was shown to be 96% pure by HPLC.

MS (30 ev): 427 (M+), 253, 225, 117, 83.

Pmr (CDCl3): according to theory.

Elemental Analysis: $C_{24}H_{21}F_4N_3$ 0.1H2O: Calc: N, 9.79; C, 67.15; H, 4.97 Found: N, 9.86; C, 66.99; H, 5.09.

EXAMPLE 7

Preparation of 1-methyl-2-[2-((1,1-dimethylethoxy)carbonyl)amino-3-(1H-indol-3-yl)propanoyl]aminomethyl-5-(2'-fluorophenyl)-2,3-dihydro-1H-1,4-benzodiazepine

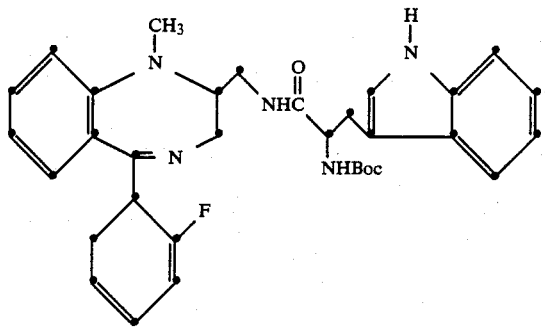

According to the method of Example 1, 1-methyl-2-aminomethyl-5-(2'-fluorophenyl)-2,3-dihydro-1H-1,4-benzodiazepine (250 mg, 0.88 mmole) and L-2-((1,1-dimethylethoxy)carbonyl)amino-3-(1H-indol-3-yl)propanoic acid (268 mg, 0.88 mmole) were combined with 4 ml of dry methylene chloride, and 1-ethyl-3-(3-dimethylaminopropyl)carbodiimide hydrochloride (169 mg, 0.88 mmole) was added to this mixture. After pH-adjustment, overnight stirring, dilution and washing, rotoevaporation of the dried extracts of the reaction afforded 500 mg of a foam which was purified by silica gel chromatography (chloroform-ethanol-ammonia elution, 90:10:1 v/v) to give the analytical sample (270 mg) which was 98% pure by HPLC; m.p. 124° C.

MS (FAB): 570 (M++H), 514, 253.

Pmr (CDCl3): according to theory.

Elemental Analysis: $C_{33}H_{36}FN_5O_3$ 0.3H2O: Calc: N, 12.17; C, 68.91; H, 6.42 Found: N, 12.15; C, 68.91; H, 6.71.

EXAMPLE 8

Preparation of 1-methyl-2-[(2-methylpropoxy)carbonyl]aminomethyl-5-(2'-fluorophenyl)-2,3-dihydro-1H-1,4-benzodiazepine

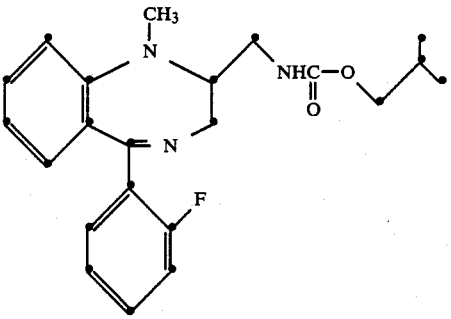

According to the method of Example 1, 1-methyl-2-aminomethyl-5-(2'-fluorophenyl)-2,3-dihydro-1H-1,4-benzodiazepine (250 mg, 0.88 mmole) and isobutyl chloroformate (114 µl, 0.88 mmole) were combined with 4 ml of dry methylene chloride, and 97 µl of N-methylmorpholine (0.88 mmole) at −5° C. was added to the mixture. The resulting reaction mixture was allowed to warm to room temperature over 2 hours, and after dilution and washing, rotoevaporation of the dried extracts of the reaction afforded 230 mg of an oil which was purified by silica gel chromatography (ethyl acetate-hexane elution, 7:3 v/v) to give the analytical sample (120 mg) which was 98% pure by HPLC.

MS (20 ev): 398 (M+), 383, 281, 253, 225.

Pmr (CDCl3): according to theory.

Elemental Analysis: $C_{22}H_{26}FN_3O_2$ $0.6H_2O$: Calc: N, 10.65; C, 67.02; H, 6.95 Found: N, 10.65; C, 66.92; H, 6.90.

EXAMPLE 9

Preparation of
1-methyl-2-[2-amino-3-(1H-indol-3-yl)propanoyl-]aminomethyl-5-(2'-fluorophenyl)-2,3-dihydro-1H-1,4-benzodiazepine dihydrochloride sesquihydrate

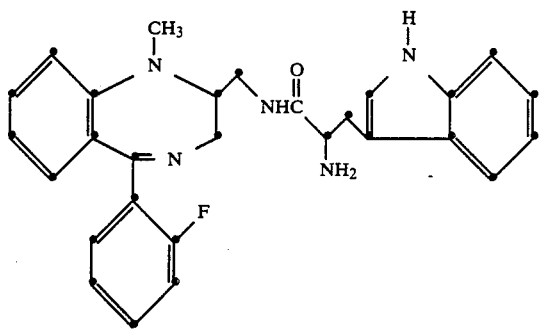

1-Methyl-2-[2-((1,1-dimethylethoxy)carbonyl)amino-3-(1H-indol-3-yl)propanoyl]aminomethyl-5-(2'-fluorophenyl)-2,3-dihydro-1H-1,4-benzodiazepine (50 mg, 0.08 mmole) was dissolved in 2 ml of ethyl acetate, cooled to 0° C. and treated with hydrogen chloride gas for 1 hour. The solvent and excess hydrogen chloride were removed under reduced pressure to give the product as a foam which was 96% pure by HPLC.

MS (FAB): 470 (M++H), 185.

Pmr (CD3OD): according to theory.

Elemental Analysis: $C_{28}H_{30}Cl_2FN_5O$ $1.5H_2O$: Calc: N, 12.30; C, 59.04; H, 5.79 Found: N, 11.67; C, 59.23; H, 5.89.

EXAMPLE 10

Preparation of
1-methyl-2-(2-methoxy-2-trifluoromethyl-2-phenylacetyl)aminomethyl-5-(2'-fluorophenyl)-2,3-dihydro-1H-1,4-benzodiazepine

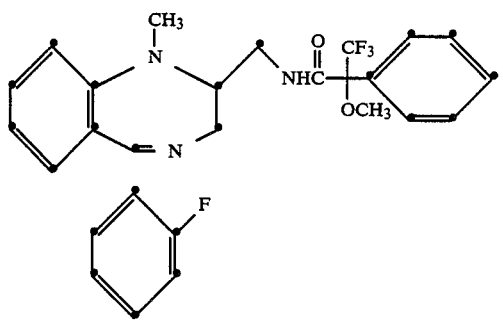

According to the method of Example 1, 1-methyl-2-aminomethyl-5-(2'-fluorophenyl)dihydro-1H-1,4-benzodiazepine (250 mg, 0.88 mmole) and (−)-L-methoxy-L-(trifluoromethyl)phenylacetic acid (222 mg, 0.95 mmole) were combined with 4 ml of dry methylene chloride, and 1-ethyl-3-(3-dimethylaminopropyl)carbodiimide hydrochloride (182 mg, 0.95 mmole) was added to the mixture. After pH-adjustment, overnight stirring, dilution and washing, rotoevaporation of the dried extracts afforded 400 mg of a solid, as a mixture of diasteriomers, which was purified by silica gel chromatography (ethyl acetate-hexane elution, 2:3 v/v) to give the analytical sample (200 mg) which was pure by HPLC.

MS (20 ev): 499 (M+), 253, 225, 189.

Pmr (CDCl3): according to theory.

Elemental Analysis: $C_{27}H_{25}F_4N_3O_2$ $0.75H_2O$: Calc: N, 8.19; C, 63.21; H, 5.20 Found: N, 8.08; C, 63.12; H, 4.99.

EXAMPLE 11

Preparation of
1-methyl-2-[2(S)-((1,1-dimethylethoxy)carbonyl)amino-3-acetamidomethylmercaptopropanoyl]aminomethyl-5-(2'-fluorophenyl)-2,3-dihydro-1H-1,4-benzodiazepine hemihydrate

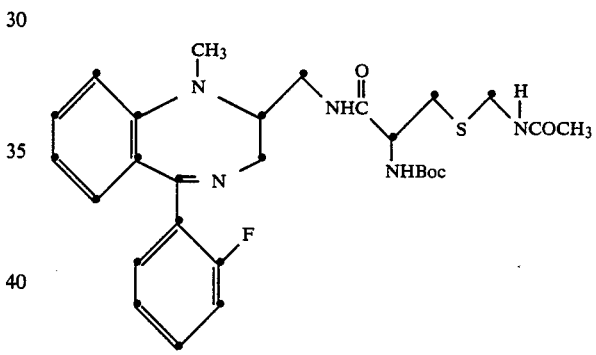

According to the method of Example 1, 1-methyl-2-aminomethyl-5-(2,-fluorophenyl)-2,3 -dihydro-1H-1,4-benzodiazepine (620 mg, 2.18 mmole) and 2(S)-((1,1-dimethylethoxy)carbonyl)amino-3-acetamidomethyl-mercaptopropanoic acid (643 mg, 2.20 mmole) were combined with 10 ml of dry methylene chloride, and 1-ethyl-3-(3-dimethylaminopropyl)carbodiimide hydrochloride (422 mg, 2.20 mmole) was added to the mixture. After pH-adjustment, overnight stirring, dilution and washing, rotoevaporation of the dried extracts afforded 1 g of crude product which was purified by silica gel chromatography (chloroform-ethanol elution, 94:6 v/v) to give the analytical sample (420 mg) which was 96% pure by HPLC, m.p. 100°–103° C.

MS (FAB): 558 (M++H).

Pmr (CDCl3): according to theory.

Elemental Analysis: $C_{28}H_{36}FN_5O_4S$ $0.5H_2O$: Calc: N, 12.36; C, 59.34; H, 6.58 Found: N, 12.47; C, 59.14; H, 6.66.

EXAMPLE 12

Preparation of 1-methy-2-benzoylsuccinoylaminomethyl-5-(2'-fluorophenyl)-2,3-dihydro-1H-1,4-benzodiazepine

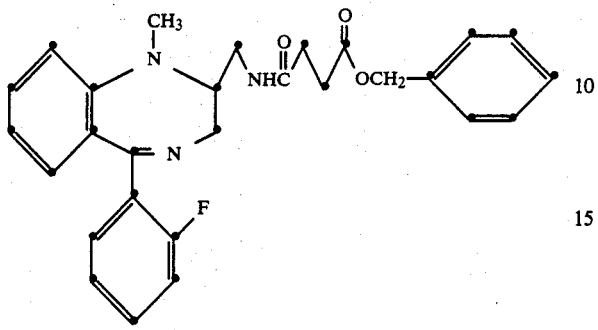

According to the method of Example 1, 1-methyl-2-aminomethyl-5-(2'-fluorophenyl)-2,3-dihydro-1H-1,4-benzodiazepine (250 mg, 0.88 mmole) and benzylsuccinic acid (185 mg, 0.88 mmole) were combined with 5 ml of dry methylene chloride, and 1-ethyl-3-(3-dimethylaminopropyl)carbodiimide hydrochloride (169 mg, 0.88 mmole) was added to the mixture. After pH-adjustment, overnight stirring, dilution and washing, rotoevaporation of the dried extracts afforded 360 mg of an oil which was purified by silica gel chromatography (chloroform-ethanol elution, 95:5 v/v) to give the analytical sample (140 mg) which was 88% pure by HPLC.

MS (20 ev): 473 (M+), 365, 253, 238, 225, 108.

Pmr (CDCl$_3$): according to theory.

Elemental Analysis: $C_{28}H_{28}FN_3O_3$ 0.3H$_2$O: Calc: N, 8.77; C, 70.21; H, 6.01 Found: N, 8.93; C, 70.35; H, 6.08.

EXAMPLE 13

Preparation of 1-methyl-2-(acetamidomethylmercaptoacetyl)aminomethyl-5-(2'-fluorophenyl-2,3-dihydro-1H-1,4-benzodiazepine hydrate

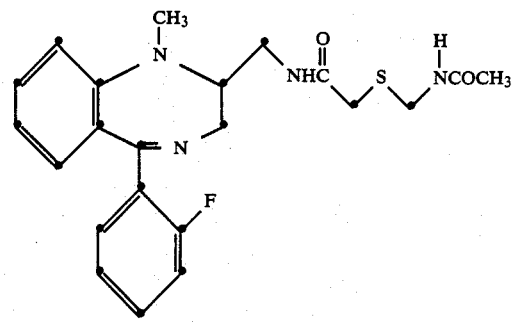

According to the method of Example 1, 1-methyl-2-aminomethyl-5-(2'-fluorophenyl)-2,3-dihydro-1H-1,4-benzodiazepine (1.96g, 6.9 mmole) and acetamidomethylmercaptoacetic acid (1.26 g, 7.7 mmole) were combined with 25 ml of dry methylene chloride and 1-ethyl-3-(3-dimethylaminopropyl)carbodiimide hydrochloride (1.48 g, 7.7 mmole) was added to the mixture. After pH-adjustment, overnight stirring, dilution with 250 ml of ethyl acetate and washing, rotoevaporation of the dried extracts afforded 2.63 g of an oil which was purified by silica gel chromatography (chloroform-ethanol-ammonia elution, 90:10:1 v/v) to give the analytical sample (850 mg) which was 95% pure by HPLC.

MS (30 ev): 428 (M+), 253, 225.

Pmr (CDCl$_3$): according to theory.

Elemental Analysis: $C_{22}H_{25}FN_4O_2S$ H$_2$O: Calc: N, 12,54; C, 59.17; H, 6.09 Found: N, 12.68; C, 59.37; H, 5.89.

EXAMPLE 14

Preparation of 1-methyl-2-(3-thiophenecarbonyl)aminomethyl-5-(2'-fluorophenyl)-2,3,4,5-tetrahydro-1H-1,4-benzodiazepine

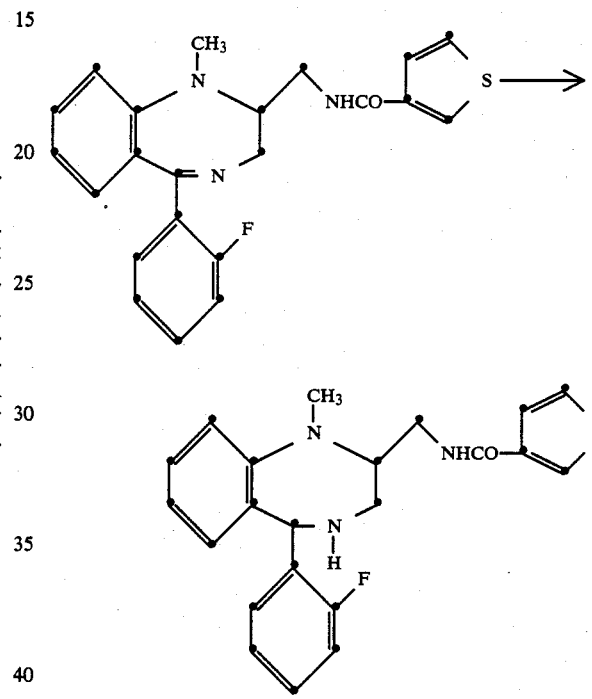

1-methyl-2-(3-thiophenecarbonyl)aminomethyl-5-(2'-fluorophenyl)-2,3-dihydro-1H-1,4-benzodiazepine (440 mg, 1.12 mmole) was dissolved in 35 ml of glacial acetic acid and the magnetically stirred solution was cooled to 10° C. and treated with 282 mg (4.48 mmole) of sodium cyanoborohydride. The reaction mixture was stirred for five minutes and then poured into 200 ml of water. The resulting suspension was extracted with ethyl acetate (4×50 ml) and the combined organic extracts were washed with 10% sodium bicarbonate solution (3×50 ml) and brine (50 ml). Rotoevaporation of the dried extracts (Na$_2$SO$_4$) afforded 450 mg of the crude product as a solid which is a mixture of diasteriomers. The analytical sample was obtained via chromatography on silica gel (95:5:0.5 chloroform-methanol-ammonia elution).

Elemental Analysis: $C_{22}H_{22}FN_3OS$ 0.2H$_2$O: Calc: N, 10.52; C, 66.20; H, 5.65 Found: N, 10.95; C, 66.12; H, 5.63.

HPLC (97% pure).

Mass Spec. (20 ev): (M+ −395), 380, 255 (Base Peak), 226, 212, 83.

Pmr (CDCl$_3$): 3.11 (3H, s, CH$_3$), 3.23 (1H, dxt, J=17, 6), 3.25 (1H, dxd, J=14, 3), 3.33 (1H, dxd, J=14, 3), 3.41 (1H, m), 3.52 (1H, dxt, J=17, 6), 5.28 (1H, s), 6.53 (1H, s), 6.55 (1H, s), 6.78 (1H, t, J=8), 7.09 (1H, t, J=8), 7.11 (1H, t, J=8), 7.25 (4H, m), 7.50 (1H, t, J=8), 7.69 (1H, dxd, J=3, 1).

EXAMPLE 15

CCK Activity Assessment

The compounds produced in the preceding examples were tested for antagonism to CCK receptor binding in both the pancreas and brain using the methods described above, with the following results:

| Compound from Examples | $IC_{50}$ ($\mu M$) CCK, Pancreas | $IC_{50}$ ($\mu M$) CCK, Brain |
|---|---|---|
| 1 | 0.16 | 14.00 |
| 2 | 0.45 | 23.00 |
| 3 | 0.60 | ca.100 |
| 4 | 1.00 | 56.00 |
| 5 | 1.60 | ca.100 |
| 6 | 2.20 | ca.100 |
| 7 | 4.10 | 38.60 |
| 8 | 5.80 | ca.100 |
| 9 | 11.60 | ca.100 |
| 10 | 13.00 | ca.100 |
| 11 | 24.00 | ca.100 |
| 12 | 45.00 | 55.00 |
| 13 | 100.00 | ca.100 |
| 14 | 4.80 | ca.100 |

The $IC_{50}$ values (the concentrations required to cause inhibition of 50% of the $^{125}$I-CCK binding) in the pancreas demonstrate the compounds of the present invention are from about 10 times to about 1000 times more potent than previously known compounds, and thus demonstrate significantly improved antagonism to the function of CCK.

What is claimed is:

1. 2-Substituted-aminomethyl-1, 4-benzodiazepines of formula I:

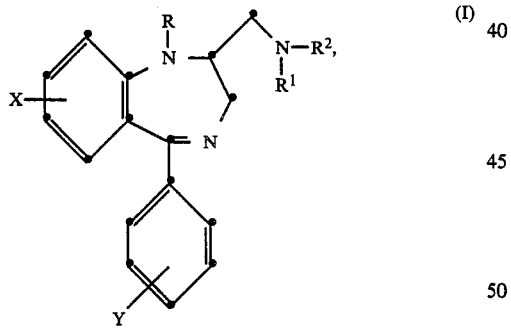

wherein:
X=one or two of the substituents: F, Cl or Br; $C_1$–$C_4$- straight or branched-chain alkyl; $C_1$–$C_4$-alkoxy; $C_1$–$C_4$-alkylthio; nitro; cyano; amino; or trifluoromethyl, and may be attached at either or both the 7- and/or 8-positions;
Y=independently, the same as X, and may be attached at any of positions 2–6 on the aromatic ring;
R=H, $C_1$–$C_4$-alkyl, cyclo-$C_3$–$C_5$-alkyl, $C_1$–$C_4$-alkenyl, or acetyl;
$R^1$=H, $C_1$–$C_4$-alkyl or cyclo-$C_3$–$C_5$-alkyl;

$R^2$ = —CH—$R^3$, where $R^3$ = $(CH_2)_n$—$C_1$—$C_4$—alkyl,
         |
         $CO_2R^4$ —$(CH_2)_n$—2-indole,
—$(CH_2)_n$—3-indole, or
—$(CH_2)_n$—phenyl (unsubstituted or mono- or disubstituted, where the substituents are as defined for X, above);
n = 0–4; and
$R^4$ = H or $C_1$—$C_4$—alkyl; or $=$ —C(=O)—$R^5$, where $R^5$ = —CH—$R^6$, wherein $R^6$ =
                                  |
                                  $NHR^7$
$(CH_2)_n$—2-indole or
$(CH_2)_n$—3-indole, where n = 0–4; and $R^7$ = H, $COOR^8$, or —$CR^8$(=O), where $R^8$ =
$C_1$—$C_4$—alkyl;
= —$(CH_2)_m SCH_2NHCOCH_3$,
  where m = 1–4;

= [heterocycle with $(CH_2)_n$ attachment, $Z$, $X$]

wherein Z = O, S or NR, $(CH_2)_n$ is attached at the 2- or 3-position, and R, n and X are as defined above;

= [heterocycle with $(CH_2)_n$, Z]

wherein $(CH_2)_n$ is attached at the 4- or 5-position, and n and Z are as defined above;

= $(CH_2)_m CO_2 CH_2$phenyl, wherein m is as defined above;
= —O—$C_1$—$C_4$—alkyl;
= —CHOHC$_6$H$_5$; or

= CF$_3$
  —C—C$_6$H$_5$;
  OCH$_3$ or of formula II:

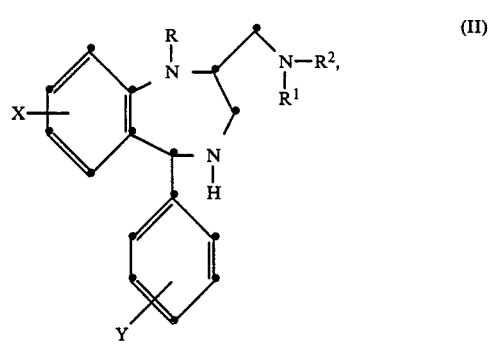

wherein:
X, Y, R, $R^1$ and $R^2$ are as defined above;
The optical isomers of formula I, or pharmaceutically-acceptable salts of the compounds of a formulae I or II.

2. The 2-substituted-aminomethyl-1, 4-benzodiazepines, according to claim 1, wherein in formula I: X is F or Cl; R is H or $C_1$–$C_4$-alkyl; $R^1$ is H; $R^2$ is

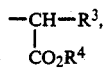

wherein R³ is —CH₂-phenyl or CH₂-2 or 3-indoel, and R⁴ is C₁–C₄-alkyl; or R² is

wherein R⁵ is

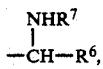

where R⁶ is CH₂-2-indole or CH₂-3-indole and R⁷ is H, —COOR⁸, or

wherein R⁸ is C₁–C₄-alkyl; or R⁵ is

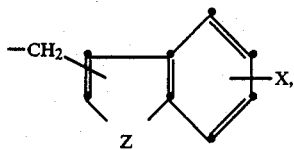

wherein Z is O, S or NR, and X, R and n are as defined above; or R⁵ is

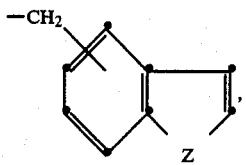

wherein Z is as defined above; or R⁵ is —CHOHC₆H₅, and in formula II: X if F or Cl; R is H or C₁–C₄-alkyl; R¹ is H; R² is

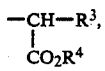

wherein R³ is —CH₂-phenyl or CH₂-2 or 3-indole, and R⁴ is C₁–C₄-alkyl; or R² is

wherein R⁵ is

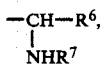

where R⁶ is CH₂-2-indole or CH₂-3-indole and R⁷ is H; —COOR⁸, or

wherein R⁸ is C₁–C₄-alkyl; or R⁵ is

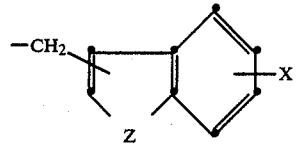

wherein Z is O, S or NR, and X and R are as defined above; or R⁵ is

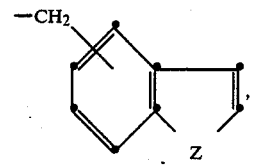

wherein Z is as defined above; or R⁵ is —CHOHC₆H₅.

3. 2-Substituted-aminomethyl-1,4-benzodiazepines according to claim 1, selected from one or more members of the group consisting of 1-methyl-2-(2'-indolecarbonyl)aminomethyl-5-(2'-fluorophenyl)-2,3-dihydro-1H-1,4-benzodiazepine, 1-methyl-2-(4-thianaphthenemethylcarbonyl)aminomethyl-5-(2'-fluorophenyl)-2,3-dihydro-1H-1,4-benzodiazepine, 1-methyl-2-(2-L-hydroyxy-2-phenylacetyl)aminomethyl-5-(2'-fluorophenyl)-2,3-dihydro-1H-1,4-benzodiazepine, 1-methyl-2-(1H-indol-3-yl)methylcarbonylaminomethyl-5-(2'-fluorophenyl)-2,3-dihydro-1H-1,4-benzodiazepine, 1-methyl- 2-[1-(S)-1-methoxycarbonyl-2-phenylethylamino]methyl-5-(2'-fluorophenyl)-2,3-dihydro-1H-1,4-benzodiazepine, 1-methyl-2-[2-((1,1-dimethylethoxy)carbonyl)amino-3-(1H-indol-3-yl)propanoyl]aminomethyl-5-(2'-fluorophenyl)-2,3-dihydro-1H-1,4-benzodiazepine, 1-methyl-2-[(2-methylpropoxy)carbonyl]aminomethyl-5-(2'-fluorophenyl)-2,3-dihydro-1H-1,4-benzodiazepine, 1-methyl-2-[2-amino-3-(1H-indol-3-yl)propanoyl]aminomethyl-5-(2'-fluorophenyl)-2,3-dihydro-1H-1,4-benzodiazepine, 1-methyl-2-(2-methoxy-2-trifluoromethyl-2-phenylacetyl)aminomethyl-5-(2'-fluorophenyl)-2,3-dihydro-1H-1,4-benzodiazepine, 1-methyl-2-[2-(S)-((1,1-dimethylethoxy)carbonyl)amino-3-acetamidomethylmercaptopropanoyl]aminomethyl-5-(2'-fluorophenyl)-2,3-dihydro-1H-1,4-benzodiazepine, 1-methyl-2-benzylsuccinoylaminomethyl-5-(2'-fluorophenyl)-2,3-dihydro-1H-1,4-benzodiazepine, 1-methyl-2-(acetamidomethylmercaptoacetyl)aminomethyl-5-(2'-fluorophenyl)-2,3-dihydro-1H-1,4-benzodiazepine, 1-methyl-2-(2'-indolecarbonyl) aminomethyl-5-(2'-fluorophenyl)-2,3,4,5-tetrahydro-1H-1,4-benzodiazepine, 1-methyl-2-(4-thianaphthenemethylcarbonyl)aminomethyl-5-(2'-fluorophenyl)-2,3,4,5-tetrahydro-1H-1,4-benzodiazepine, 1-methyl-2- (2-L-hydroxy-2-phenylacetyl)aminomethyl-5-(2'-fluorophenyl)-2,3,4,5-tetrahydro-1H-1,4-benzodiazepine, 1-methyl-2-(1H-indol-3-yl)methylcarbonylaminomethyl-5-(2'-fluorophenyl)-2,3,4,5-tetrahydro-1H-1,4-benzodiazepine.

4. A composition comprising a pharmaceutically-effective amount for antagonism of the function of cholecystokinins in mammals of one or more 2-substituted-aminomethyl-1,4-benzodiazepines according to claim 1, optical isomers thereof, or pharmaceutically-acceptable salts thereof and a pharmaceutically-acceptable carrier.

5. A composition according to claim 4, further comprising an adjuvant.

6. A composition according to claim 4 or claim 5, wherein the 2-substituted-aminomethyl-1,4-benzodiazepins are selected from one or more members of the group consisting of 1-methyl-2-(2'-indolecarbonyl)aminomethyl-5-(2'-fluorophenyl)-2,3-dihydro-1H-1,4-benzodiazepine, 1-methyl-2-(4-thianaphthenemethylcarbonyl)aminomethyl-5-(2'-fluorophenyl)-2,3-dihydro-1H-1,4-benzodiazepine, 1-methyl-2-(2-L-hydroxy-2-phenylacetyl)aminomethyl-5-(2'-fluorophenyl)-2,3-dihydro-1H-1,4-benzodiazepine, 1-methyl-2-(1H-indol-3-yl)methylcarbonylaminomethyl-5-(2'-fluorophenyl)-2,3-dihydro-1H-1,4-benzodiazepine, 1-methyl-2-[1-(S)-1-methoxycarbonyl-2-phenylethylamino]methyl-5-(2'-fluorophenyl)-2,3-dihydro-1H-1,4-benzodiazepine, 1-methyl-2-[2-((1,1-dimethylethoxy)carbonyl)amino-3-(1H-indol-3-yl)propanoyl]aminomethyl-5-(2'-fluorophenyl)-2,3-dihydro-1H-1,4-benzodiazepine, 1-methyl-2-[(2-methylpropoxy)carbonyl]aminomethyl-5-(2'-fluorophenyl)-2,3-dihydro-1H-1,4-benzodiazepine, 1-methyl-2-[2-amino-3-(1H-indol-3-yl)propanoyl]aminomethyl-5-(2'-fluorophenyl)-2,3-dihydro-1H-1,4-benzodiazepine, 1-methyl-2-(2-methoxy-2-trifluoromethyl-2-phenylacetyl)aminomethyl-5-(2'-fluorophenyl)-2,3-dihydro-1H-1,4-benzodiazepine, 1-methyl-2-[2-(S)-((1,1-dimethylethoxy)carbonyl)amino-3-acetamidomethylmercaptopropanoyl]aminomethyl-5-(2'-fluorophenyl)-2,3-dihydro-1H-1,4-benzodiazepine, 1-methyl-2-benzylsuccinoylaminomethyl-5-(2'-fluorophenyl)-2,3-dihydro-1H-1,4-benzodiazepine, 1-methyl-2-(acetamidomethylmercaptoacetyl)aminomethyl-5-(2'-fluorophenyl)-2,3-dihydro-1H-1,4-benzodiazepine, 1-methyl-2-(2'-indolecarbonyl)aminomethyl-5-(2'-fluorophenyl)-2,3,4,5-tetrahydro-1H-1,4-benzodiazepine, 1-methyl-2-(4-thianaphthenemethylcarbonyl)aminomethyl-5-(2'-fluorophenyl)-2,3,4,5-tetrahydro-1H-1,4-benzodiazepine, 1-methyl-2-(2-L-hydroxy-2-phenylacetyl)aminomethyl-5-(2'-fluorophenyl)-2,3,4,5-tetrahydro-1H-1,4-benzodiazepine, 1-methyl-2-(1H-indol-3-yl)methylcarbonylaminomethyl-5-(2'-fluorophenyl)-2,3,4,5-tetrahydro-1H-1,4-benzodiazepine.

7. A composition according to claim 4 or claim 5, wherein the pharmaceutically-effective amount is from about 0.05 mg/kg to about 100 mg/kg, administered in single or divided doses.

8. A composition according to claim 7, wherein the pharmaceutically-effective amount is from about 0.5 mg/kg to about 20 mg/kg.

9. A composition according to claim 4 or claim 5, wherein the mammals are humans.

* * * * *